United States Patent [19]

Stenfors

[11] Patent Number: 5,479,470
[45] Date of Patent: Dec. 26, 1995

[54] X-RAY EXAMINATION APPARATUS

[75] Inventor: Per Stenfors, Spanga, Sweden

[73] Assignee: Siemens Elema AB, Solna, Sweden

[21] Appl. No.: 355,958

[22] Filed: Dec. 14, 1994

[30] Foreign Application Priority Data

Dec. 22, 1993 [SE] Sweden ............................ 9304249

[51] Int. Cl.⁶ ............................................. H05G 1/02
[52] U.S. Cl. .................... 378/196; 378/195; 378/197
[58] Field of Search ............................ 378/193, 195, 378/196, 197, 198

[56] References Cited

U.S. PATENT DOCUMENTS

| 4,922,512 | 5/1990 | Lajus et al. | 378/197 |
| 4,987,585 | 1/1991 | Kidd et al. | 378/197 |
| 5,386,453 | 1/1995 | Harrawood et al. | 378/198 |

FOREIGN PATENT DOCUMENTS

| 0224886 | 6/1987 | European Pat. Off. . |
| 0375552 | 6/1990 | European Pat. Off. . |

OTHER PUBLICATIONS

Geenral Electric Brochure for "Advantx L/C" multi-axis cardiovascular imaging system (1989).
Philips Brochure for "Integris BN 3000" and Integris BV 3000 Neurological and Angiographic Radiological Systems (1993).
Siemens Brochure for "ANGIOSTAR" Universal system for film and digital angiography.
Siemens Brochure for "COROSKOP HS" High-speed Angiocardiography System.

*Primary Examiner*—David P. Porta
*Assistant Examiner*—Don Wong
*Attorney, Agent, or Firm*—Hill, Steadman & Simpson

[57] ABSTRACT

An x-ray examination apparatus has a stand composed of at least one upright column, a holder for a curved carrier rotatable around a horizontal axis and connected to the column, an x-ray tube and a receptor being secured to the holder, a fastening means for the stand, and an arm that connects the stand to the fastening means. One end of the arm is rotatable around an axis at the fastening means. The apparatus also includes an examination table that is displaceable at least along a center line. In order to provide an apparatus having a stand that is comparatively simple in structure and that has an extraordinarily large movement range and that can displace the center line of the x-ray tube and receptor between two points on the center line of the examination table that lie comparatively far apart without a table displacement, the fastening means is placed such that the axis thereof does not coincide with the center line of the examination table, and the other end of the arm is rotatably connected to a vertical axis arranged at the column. A mechanism given a rotation of the arm around the axis of the fastening means, turns the stand around the axis at the column such that the center line of the x-ray tube and receptor intersects the center line of the examination table in at least two angular positions of the arm, whereby the stand—as viewed from above—is in axial alignment with the center line of the examination table in the first angular position of the arm and the stand describes an angle with this center line in the second angular position of the arm.

6 Claims, 2 Drawing Sheets

X-RAY EXAMINATION APPARATUS

BACKGROUND OF THE INVENTION

1. Field Of the Invention

The present invention is directed to an x-ray examination apparatus of the type having a stand composed of at least one base, a holder for a curved carrier rotatable around a horizontal axis and connected to the base, an x-ray tube and an x-ray receptor (detector) being secured to the carrier, a fastening means for the stand and an arm that connects the stand to the fastening means, with the one end of the arm being rotatable around an axis at the fastening means, as well as having an examination table that is displaceable at least along its center line.

2. Description of the Prior Art

It is of significance in conjunction with radiological heart examinations that the x-ray tube and the receptor be able to sweep the upper body of the patient to the groin. It is also desirable in other examinations to sweep the entire length of the patient. In such examinations, the apparatus stand can be attached to the long side of the examination table and can be displaced parallel with the examination table, permitting the aforementioned patient region to be reached without difficulty with the x-ray tube and the receptor. Such an examination apparatus is known from the Siemens brochure "ANGIOSTAR" wherein the stand is displaceable in floor rails. Given such an examination apparatus, the physician has extremely good access to the patient at the head end and at the long side of the table but, of course, not from the side at which the stand is attached.

A stand attached at the head end is known in another type of x-ray examination apparatus wherein the inside diameter of the curved carrier defines how far the x-ray tube and the receptor can sweep the body of the patient when the head end of the examination table is placed in the carrier arc between the x-ray tube and the receptor tightly against the holder of the carrier arc. Such an examination apparatus is described in the Siemens brochure "COROSKOP HS". The problem involving motion limitations of the x-ray tube and of the receptor due to the shape of the carrier arc is partially resolved given this examination apparatus because the stand, which is placed on the floor, is rotatable around a vertical axis and can be combined with an examination table suspended at the ceiling, which can be displaced in a longitudinal direction as well as laterally relative to the longitudinal direction, or can be combined with an examination table attached to the floor that is rotatable around a vertical axis. The position of the examination table must be set with every rotation of the stand around the vertical axis.

The brochure "Advantx L/C" of GE Medical Systems describes an x-ray examination apparatus of the type initially described. The axis of the fastening means around which the arm is rotatable is applied to the floor and, as viewed from above, is attached on the imaginary center line of the examination table under the head end of the table. Due to the arm that extends under the table, the stand together with the carrier for the x-ray tube and the receptor can be turned around the axis of the fastening means from a position wherein the carrier is attached to the head end of the table into a further position wherein the carrier is arranged at an angle of 90° relative to the longitudinal direction of the table. The stand is constructed such that the center line between the x-ray tube and the receptor lies axially aligned with the axis in the fastening means given a vertical adjustment. The imaginary center line between the x-ray tube and the receptor is therefore always fixed in the same isocenter given a rotation of the stand around the axis of the fastening means. The available amount of longitudinal displacement of the table determines how large the part of the patient that can be examined is. Since the arm placed at the floor is comparatively broad and high in the region of the axis of the fastening means, the physician can bump against the arm with his or her feet during the examination; this can be disturbing. Due to the position and size of the arm, the carrier for the x-ray tube and the receptor cannot be lowered down to the floor given a vertical attitude. In such a vertical attitude, a lowering of the x-ray tube and of the receptor by 4-5 cm, this being estimated to be the thickness of the arm, can be critical in some instances in order to obtain a good exposure.

The Philips brochure "Integris BN 3000 und Integris BV 3000" shows and describes a further stand that can change between a head position and a side position. This stand is constructed such that the holder for the carrier to which the x-ray tube and the receptor are secured is directly attached to the fastening means at the floor and can be turned around the vertical axis thereof. The axis of the fastening means is arranged under the head end of the examination table and, as viewed from above, is placed at the imaginary center line of the examination table. The center line of the x-ray tube and of the receptor given a vertical attitude is also arranged in alignment here with the axis of the fastening means. Due to this structure, the center line for the x-ray tube and the receptor does not have an imaginary isocenter given a swiveling of the holder and of the carrier. Again, the size of the part of the patient that can be examined is also dependent on the size of the longitudinal displacement of the table. Due to the structure of the stand, this carrier also cannot be lowered down to the floor.

SUMMARY OF THE INVENTION

An object of the present invention is to provide an x-ray apparatus equipment of the type initially described having a stand with a comparatively simple structure that has an extraordinarily large movement range and that can—without the assistance of a table displacement—move the center line of the x-ray tube and of the receptor between two points on the center line of the examination table that lie comparatively far apart.

This object is inventively achieved in an x-ray examination apparatus of the type initially described wherein the fastening means is placed such that the axis thereof does not coincide with the center line of the examination table. As noted above, in an apparatus of this type, one end of the arm is rotatable around an axis of the fastening means and in accordance with the invention the other end of the arm is rotatably connected to a vertical axis arranged at the base and the apparatus has means given a rotation of the arm around the axis of the fastening means, for turning the stand around the axis of the base such that the center line of the x-ray tube and receptor intersects the center line of the examination table in at least two angular positions of the arm. The stand, viewed from above, lies in axial alignment with the center line of the examination table in the first angular position of the arm and the stand forms an angle with this center line in the second angular position of the arm. As a result, the stand can be a standard stand, for example, a C-arm type, that can be placed at the head end and is extremely simple and inexpensive. The stand occupies comparatively little space and does not disturb the physician since the base is attached outside the actual region around the examination table, and as a result the physician is provided with extremely good access to the patient. In an embodiment of the invention the rotation of the stand around the arm is implemented with a translation compared to the rotation of the arm around the fastening means such that the intersection between the center line of the x-ray tube and receptor and the center line of the examination table is shifted in the first angular position of the arm by comparison to the intersection in the second angular position of the arm. This translation gives the stand an extremely large longitudinal movement range of up to approximately 45 cm. Including a receptor movement of 17 cm, the longitudinal movement range of the examination table therefore need only be approximately 125 cm in order to be able to implement a whole body examination of a patient having a height of 187 cm.

The translation ratio between the rotation around the axis of the fastening means and the rotation of the stand around the arm is 215:180 according to the invention.

In another embodiment of the invention the means that turn the stand around the axis in the base given a rotation of the arm around the axis of the fastening means are a belt or a chain transmission between the axes of the fastening means and the base. The aforementioned means may alternatively be toothed racks, parallelogram arms or similar mechanical transmissions.

In an embodiment of the invention the stand can be brought into a standby position by turning the arm into a third angular position of the arm. In the standby position, the stand is brought into a position that lies outside the peripheral region of the examination table, thereby facilitating the preparation for an x-ray examination.

DESCRIPTION OF THE PREFERRED EMBODIMENTS

Figure 1:
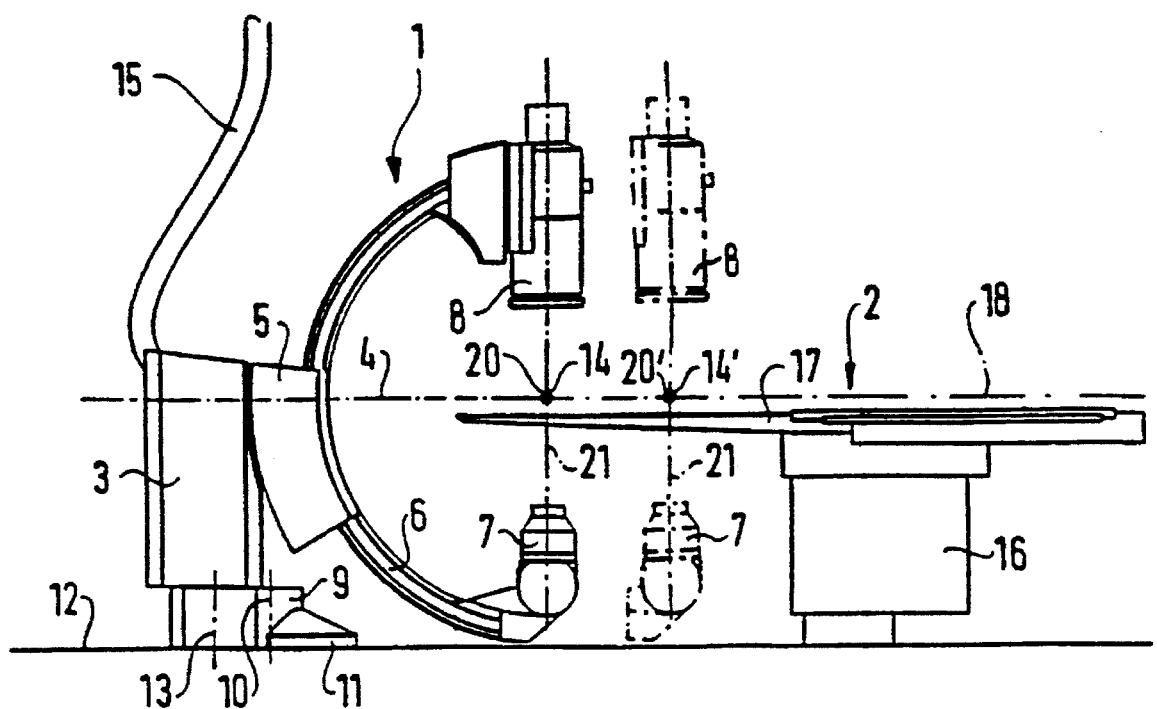
FIG. 1 is a side view of an x-ray examination apparatus constructed in accordance with the principles of the present invention of the invention.

FIG. 1 shows an x-ray examination apparatus having a stand 1 and an examination table 2. The stand 1 is composed of a base or column 3 and a holder 5 for a C-arm carrier 6 that is rotatable around a horizontal axis 4 and is connected to the column 3. An x-ray tube 7 and a receptor 8 are secured to the C-arm carrier 6. Via an arm 9, the column 3 is rotatable around an axis 10 (fastening means axis) of a fastening means 11 that is firmly connected to the floor 12. The other end of the arm 9 is rotatably connected to an axis 13 (column axis) vertically arranged in the column 3. The column 3 is also height-adjustable with known means that are therefore not shown. A central cable 15 for power supply to the components is also shown in FIG. 1. FIG. 1 also shows that the column 3 has been moved to the lowest position, whereby the C-arm 6 nearly lies against the floor 12. The x-ray tube 7 is centered relative to the receptor 8, as indicated by the center line 21. When, as shown in FIG. 1, the stand 1 is brought into an exposure position, the center line 21 intersects the imaginary extension of the axis 4 of the holder 5 in a point 14. This point 14 is an isocenter around which the x-ray tube 7 or the receptor 8 can be pivoted as the C-arm 6 is displaced in the holder 5 and is turned around the axis 4. The examination table 2, which is secured to the floor in this exemplary embodiment, is composed of a base 16 and a tabletop 17 that is at least displaceable in its longitudinal direction along a center line 18. When the stand 1, as shown in this example, is brought into what is referred to as a head-placed position, this center line 18 is in axial alignment with the axis 4 of the holder 5. The dot-dash version of the x-ray tube 7 and the receptor 8 in FIG. 1 shall be described in greater detail in conjunction with FIG. 3.

The axes 10 and 13 do not coincide, and preferably do not intersect, i.e., they are parallel. The axes 10 and 13 may, however, be very slightly non-parallel, in which case they would theoretically intersect, with the deviation from precise parallelism being insufficient to affect the intended operation.

Figure 2:
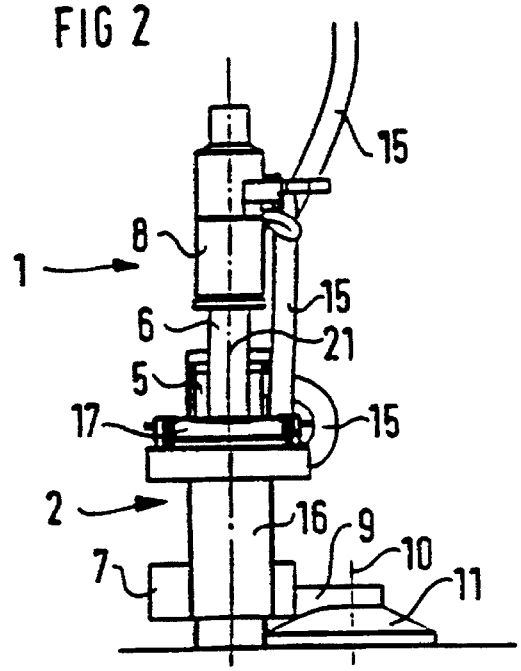
FIG. 2 is a front view of the x-ray examination apparatus of FIG. 1.
Figure 3:
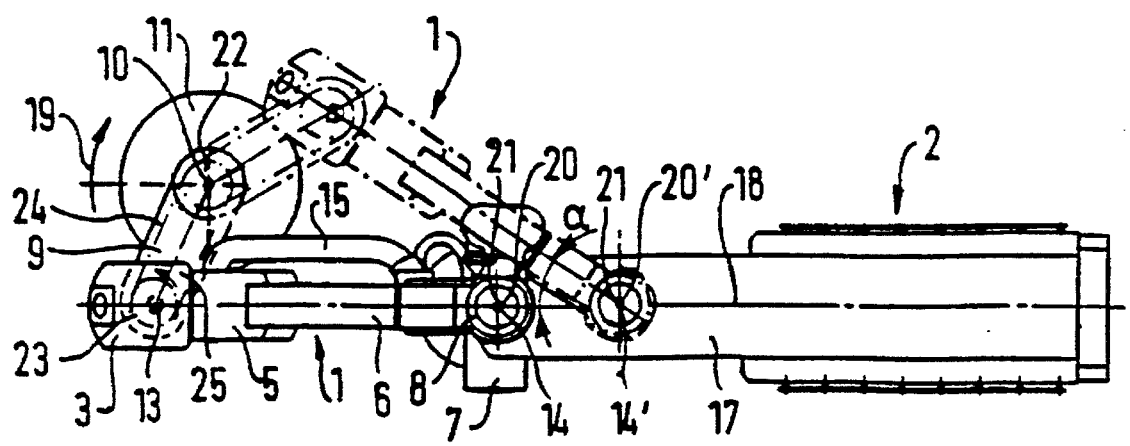
FIGS. 3 and 4 are respective plan views of the x-ray apparatus of FIGS. 1 and 2, wherein the stand has been brought into different positions.

In a front view of the x-ray examination apparatus, FIG. 2 shows a placement of the stand 1 wherein the stand is brought into a head-placed position, whereby the stand 1 with the C-arm 6 is in axial alignment—as viewed from above—with the center line 18 of the table 2, this being shown in greater detail in conjunction with FIG. 3. FIG. 2 also shows that the fastening means 11 is placed such that the axis 10 does not intersect the center line 18 of the examination table 2.

In FIG. 3, wherein the x-ray examination apparatus is shown in a plan view, the stand 1 is shown in a head-placed position that has already been set forth in conjunction with FIG. 2. FIG. 3 clearly shows that the stand 1, and thus the axis 4 of the holder 5 as viewed from above lie in axial alignment with the center line 18 of the examination table 2. It is also clearly shown in FIG. 3 that the fastening means 11 together with the axis 10 around which the arm 9 of the stand 1 is turned lie outside the center line 18 of the examination table 2. Given a rotation of the stand 1 or of the arm 9 around the axis 10 in the direction of the arrow 19, the stand 1 is displaced into a position by means described later, this position describing an angle α with the center line 18 of the examination table 2. The dot-dash contours of the stand 1 show this angular position. In this latter angular position, the center line 21 for the x-ray tube 7 and the receptor 8 intersects the center line 18 of the examination table 2 in a point 20'. The rotation of the stand 1 or of the axis 13 around the arm 9 compared to the rotation of the arm 9 around the axis 10 of the fastening means 11 ensues with such a translation that the intersection 20 between the center line 21 of the x-ray tube 7 and the receptor 8 and the center line 18 of the examination table 2 in the first-described angular position of the arm 9 is displaced compared to the intersection 20' in the second angular position of the arm, i.e. in the position wherein the stand describes an angle with the center line 18 of the examination table 2. The intersection points 20 or 20' in this example are respectively coincident congruent with the isocenters 14 and 14' in the two angular positions of the arm 9. This displacement of the intersection point 20 and the displacement of the isocenter 14 as well are shown by the dot-dash contours of the x-ray tube 7 and of the receptor 8 having the center line 21 in FIG. 1. The spacing between the axis 10 of the fastening means 11 and the intersection 20, in the second angular position of the arm 9 due to the described movement of the stand around the axis 10 of the fastening means 11 is greater than the spacing from the intersection 20 in the first angular position of the arm 9.

The means for implementing the described movement of the stand are, for example, a drive loop, such as a belt or chain transmission, between the axis 10 (i.e., a shaft) of the fastening means 11 and the axis (or shaft) 13 of the column 3. The belt transmission or the chain transmission is composed of a gear wheel 22 that is firmly connected to the shaft 10. The shaft 10 in turn has a fixed connection to the fastening means 11 and to a gear wheel 23. The gear wheel 23 is in turn firmly connected to the column 3 at the shaft axis 13. A belt or chain is arranged between the gear wheels 22 and 23. The translation ratio between the rotation of the arm 9 around the axis 10 of the fastening means 11 and the rotation of the stand 1 and the column 3 with the arm 9 is 215:180. This translation ratio is achieved by the gear wheel 23 on the shaft axis 13 of the column 3 being correspondingly larger than the gear wheel 22 on the shaft axis 10 of the fastening means 11. The arm 9 can preferably be turned by means of a motor (not shown) that, for example, is arranged at the fastening means 11. When the arm 9 is turned with the motor around the axis 10 in the direction of the arrow 19, the gear wheel 23 is compelled to climb on the belt or chain 24, so that the gear wheel 23 together with the column 3 is turned in the direction of the arrow 25, this being opposite the direction of the arrow 19. Due to the successive rotation of the gear wheel 23 or of the column 3 in relationship to the movement of the arm 9, the stand 1—when it has been brought into a head-placed position— first describes a motion moving away from the examination table 2 and subsequently describes a motion approaching the examination table 2 (an obliquely proceeding motion compared to the center line 18 thereof), until the stand 1 assumes a second angular position shown in FIG. 3. After conducting an x-ray examination with the stand 1 in the second angular position of the arm, the motor turns the arm 9 in a direction that is opposite compared to the rotational motion just set forth, whereby the gear wheel 23, as already set forth, is compelled to climb on the belt or on the chain 24 but in the opposite direction, so that the stand describes a motion moving away from the examination table 2.

Figure 4:
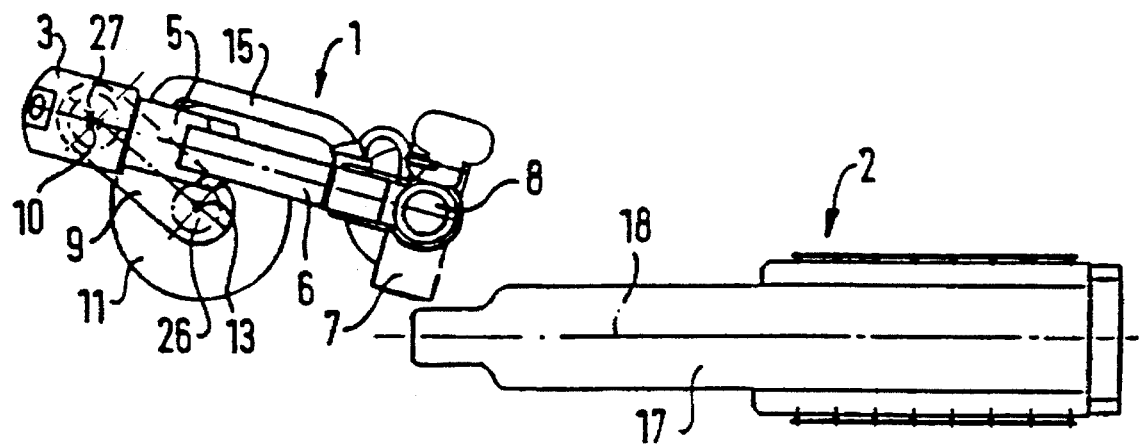

It is shown in FIG. 4 that the stand 1 can assume a standby position. Free access to the table 2 for the purpose of placing the patient on the tabletop 17 and for preparing for an examination is established in this position of the stand 1. Such a position of the stand 1 is achieved when the arm 9 is brought into a position between the abovedescribed first and second angular positions of the arm, i.e. between a head-placed and a laterally placed stand position.

As already mentioned, the means for implementing the movements of the stand can be toothed racks, parallelogram arms or similar mechanical transmissions instead of the belt or chain transmission that has been set forth.

A further possibility for controlling the stand around the fastening means 11 can be realized by two motors 26 and 27, whereby the one motor 26 is attached to the shaft axis 10 of the fastening means 11 and turns the arm 9 around the axis 10, and the further motor 27 is attached to the shaft axis 13 and turns the column 3 in relationship to the arm 9. The motors 26 and 27 are only shown in FIG. 4. With the motors 26 and 27, the motions of the arm 9 and of the stand 1 around the axis 10 of the fastening means 11 can now be controlled such that the stand 1 can at least assume the two above-described angular positions and can also assume a standby position. Control means for controlling motors in the way set forth in this exemplary embodiment are known from robotics and therefore need not be set forth in greater detail herein.

Within the scope of the invention, the column 3 should also be capable of being uncoupled from the motors that turn the arm 9. In this way, the possibility is provided of displacing the stand 1 manually into the described angular positions. The stand 1 can be locked in these positions with means that are known and that are therefore not shown. The column 3 should also be capable of being uncoupled from the gear wheel 23 on the shaft 13. As a result, the stand 1 can be turned around the axis 13 independently of the arm 9. The invention yields a stand that normally permits optimum access to the head and upper body of the patient given a head-placed position but which can be brought by the described, asymmetrically placed rotational axis 10 into a side position that, as set forth, also allows a whole-body sweep without an additional longitudinal displacement of the stand or of the table.

Although modifications and changes may be suggested by those skilled in the art, it is the intention of the inventor to embody within the patent warranted hereon all changes and modifications as reasonably and properly come within the scope of his contribution to the art.

I claim as my invention:

1. An x-ray examination apparatus comprising:

an upright column;

a curved carrier having an x-ray tube and an x-ray receptor mounted at opposite ends thereof, said x-ray tube and said x-ray receptor having a center line extending therebetween;

a holder for said curved carrier mounted on said column for permitting rotation of said curved carrier around a horizontal axis;

fastening means adapted for fastening said column to a stationary object, said fastening means having a vertical fastening means axis around which said fastening means is rotatable;

an arm connecting said fastening means to said column at a vertical column axis which does not coincide with said fastening means axis, said arm and said column being relatively rotatable around said column axis;

an examination table having a horizontally displaceable table top having an examination table center line;

said column, said arm, said fastening means, said holder and said curved carrier comprising a stand; and means for rotating said arm around said fastening means axis and for simultaneously rotating said stand around said column axis for causing said center line between said x-ray tube and said x-ray receptor to intersect said examination table center line in at least two angular positions of said arm with said stand, viewed from above, being in axial alignment with said examination table center line in a first of said angular positions and said stand forming a non-zero degree angle with said examination table center line in a second of said angular positions.

2. An x-ray examination apparatus as claimed in claim 1 wherein said means for rotating said arm and said stand comprises means for rotating said stand around said column axis with a translation compared to rotation of said arm around said fastening means axis so that an intersection of said center line between said x-ray tube and said x-ray receptor and said examination table center line in said first angular position does not coincide with an intersection of said center line between said x-ray tune and said x-ray receptor and said examination table center line in said second angular position.

3. An x-ray examination apparatus as claimed in claim 2 wherein said means for rotating said arm and said column comprises means for translating rotation of said arm around said fastening means axis relative to rotation of said column around said arm by a ratio of 215:180.

4. An x-ray examination apparatus as claimed in claim 1 wherein said fastening means axis and said column axis are disposed relative to each other so that a spacing between said fastening means axis and said intersection in said second angular position is larger than a spacing between said fastening means axis and said intersection in said first angular position.

5. An x-ray examination apparatus as claimed in claim 1 wherein said means for rotating said arm and said column includes a drive loop entrained around said fastening means axis and said column axis.

6. An x-ray examination apparatus as claimed in claim 1 further comprising means for moving said stand to a standby position by rotating said arm to bring said arm into a third angular position.

* * * * *